United States Patent [19]

Bodanszky

[11] 4,237,046
[45] Dec. 2, 1980

[54] POLYPEPTIDES AND METHODS OF PREPARATION

[76] Inventor: Miklos Bodanszky, 18035 Fernway Rd., Shaker Heights, Ohio 44122

[21] Appl. No.: 34,283

[22] Filed: Apr. 27, 1979

[51] Int. Cl.$^3$ .................... C07C 103/52; A61K 37/00
[52] U.S. Cl. ............................. 260/112.5 R; 424/177
[58] Field of Search ................ 260/112.5 R; 424/177

[56] References Cited

U.S. PATENT DOCUMENTS 3,862,927  1/1975  Said et al. ................ 260/112.5 R
4,016,258  4/1977  Said et al. ................ 260/112.5 R

OTHER PUBLICATIONS

Nabokov et al., Chem. Abst., 85, 1976, pp. 199017u.
Klausner et al., Chem. Abst., 80, 1974, pp. 77740w.
Klausner et al., Chem. Abst., 80, 1974, pp. 37441x.
Bodanszky et al., Chem. Abst., 79, 1973, pp. 487v.

Primary Examiner—Delbert R. Phillips
Attorney, Agent, or Firm—Lowe, King, Price & Becker

[57] ABSTRACT

There are disclosed active fragments of vasoactive peptides and methods of preparation. The active fragments comprise the following amino acid sequences:

(a) X-MET-ALA-VAL-$X_1$
(b) X-MET-ALA-VAL-LYS-$X_1$
(c)  X-MET-ALA-VAL-LYS-LYS-TYR-LEU-ASN-SER-Y-LEU-Z-$X_1$ wherein X is hydrogen, glutamyl, or pyroglutamyl, $X_1$ is OH or $NH_2$; Y is ILE or VAL; and Z is ASN or THR.

16 Claims, No Drawings

POLYPEPTIDES AND METHODS OF PREPARATION

BACKGROUND OF THE INVENTION

1. Field of the Invention

This invention relates to active peptide fragments of vasoactive peptides, their method of preparation, and areas of use.

2. Description of the Prior Art

The vasoactive intestinal peptide (VIP) was discovered and isolated in pure form from porcine intestines as disclosed in U.S. Pat. No. 4,119,118 of Said and Mutt. This vasoactive intestinal peptide was synthesized as reported in U.S. Pat. No. 3,862,927. A related peptide isolated from chicken or other fowl is reported in U.S. Pat. No. 4,016,258. The vasoactive intestinal peptide comprises a peptide containing a sequence of 28 amino acids in a single chain and having systemic vasodilator activity. It induces systemic hypotension and increases cardiac output on i.v. infusion. It increases hepatic arterial blood flow, increases blood sugar levels, and relaxes smooth muscle. It therefore appears to be of value in treatment of hypertension and peripheral vascular disease on parenteral administration, and as a bronchodilator on aerosol or parenteral administration.

Publications relating to the prior work regarding vasoactive intestinal peptides, are as follows:

1. S. I. Said and V. Mutt, *Science* 169, 1217 (1970)
2. S. I. Said and V. Mutt, *Nature (London)* 225, 863 (1970)
3. S. I. Said and V. Mutt, *Eur. J. Biochem.* 28, 199 (1972)
4. M. Bodanszky, Y. S. Klausner, C. Yang Lin, V. Mutt and S. I. Said, *J. Amer. Chem. Soc.* 96, 4973 (1974)
5. A. Nilsson, *Febs Lett.* 47, 284 (1974); *Ibid.* 60, 322 (1975)
6. J. M. Polak, A. G. E. Pease, J. C. Garaud and S. R. Bloom, *Gut* 15, 720 (1974)
7. S. I. Said and G. R. Faloona, *New Engl. J. Med.* 293, 155 (1975)
8. S. I. Said and R. Rosenberg, *Science* 192, 907 (1976)
9. K. Fuze, T. Hokfelt, S. I. Said and V. Mutt, *Neuroscience Lett.* 5, 241 (1977)
10. M. G. Bryant, S. R. Bloom, J. M. Polak, R. H. Albuquerque, J. Modlin and A. G. E. Pease, *Lancet* 1, 991 (1976)
11. A. Giachetti, S. I. Said, R. C. Reynolds, F. C. Koniges, *Proc. Nat. Acad. Sci. U.S.A.* 74, 3424 (1977)
12. M. Bodanszky, C. Yang Lin, A. E. Yiotakis, V. Mutt and S. I. Said, *Bioorg. Chem.* 5, 339 (1976)

The present invention provides useful polypeptide fragments of the chicken peptide and methods for their preparation.

SUMMARY OF THE INVENTION

It is accordingly one object of the present invention to provide a series of short chain peptide compounds and their method of production.

A further object of the invention is to provide short chain polypeptides which appear to have activity similar to the longer chain natural vasoactive intestinal peptides as well as being useful as intermediates for preparation of the vasoactive intestinal peptide and fowl peptide.

Other objects and advantages of the present invention will become apparent as the description thereof proceeds.

In satisfaction of the foregoing objects and advantages there are provided by this invention the free peptides, their C-terminal amides, and N-terminal pyroglutamyl derivatives which have the following amino acid sequences:

(a) X-MET-ALA-VAL-$X_1$
(b) X-MET-ALA-VAL-LYS-$X_1$
(c) X-MET-ALA-VAL-LYS-LYS-TYR-LEU-ASN-SER-Y-LEU-Z-$X_1$ wherein X is hydrogen, glutamyl or pyroglutamyl; $X_1$ is OH or $NH_2$; Y is ILE or VAL; and Z is ASN or THR.

Also provided are methods for preparation of these polypeptide fragments and their use.

DESCRIPTION OF PREFERRED EMBODIMENTS

The present invention is concerned with polypeptide fragments which, based on their structures, may have pharmacological properties like the vasoactive peptides as well as other characteristics unlike VIP. The polypeptides also have hormonal properties. The polypeptides of this invention are fragments of the polypeptides isolated from chicken or other fowl as reported in U.S. Pat. No. 4,016,258, and the polypeptides isolated from procine intestines as reported in U.S. Pat. Nos. 4,119,118 and 3,862,927. The polypeptides disclosed in these patents are closely related, differing only in the 11, 13, 26, and 28-positions. The polypeptides disclosed in these patents may be described by the following amino acid sequences:

```
  1     2     3     4     5     6     7
L-his-L-ser-L-asp-L-ala-L-val-L-phe-L-thr-
  8     9    10    11    12    13    14
L-asp-L-asn-L-tyr-L-A-L-arg-L-B-L-arg-
 15    16    17    18    19    20    21
L-lys-L-gln-L-met-L-ala-L-val-L-lys-L-lys-
 22    23    24    25    26    27    28
L-tyr-L-leu-L-asn-L-ser-L-C-L-leu-L-D-NH_2
``` where A is ser or thr; B is phe or leu; C is val or ile, and D is thr or asn.

In the specification, the amino acid components or groups of amino acid components, will be referred to by the number system indicated in the above structure.

In the above structures, the amino acid components of the peptide are of the L-form and are identified by abbreviations for convenience. These abbreviations are as follows:

| Amino Acid | Abbreviated Designation |
|---|---|
| L-pyroglutamyl | pyr |
| L-methionine | met |
| L-arginine | arg |
| L-alanine | ala |
| L-aspartic acid | asp |
| L-histidine | his |
| L-lysine | lys |
| L-leucine | leu |
| L-phenylalanine | phe |
| L-isoleucine | ile |
| L-asparagine | asn |
| L-serine | ser |
| L-tyrosine | tyr |
| L-threonine | thr |
| L-valine | val |
| L-glutamine | gln |

In the present invention, the novel polypeptides are prepared by a combination of sequential stepwise coupling (by peptide linkages) of individual amino acid components, and of block synthesis wherein various peptide segments or fragments are individually synthesized, and these segments are then coupled in proper sequence to form the desired intermediates and final products.

The pharmacological properties of vasoactive intestinal peptide (VIP) which led to its discovery and guided its isolation, e.g., relaxation of smooth muscle preparations such as rat gastric fundus and guinea pig trachea, and increase of blood flow in peripheral and splanchnic vessels, suggested a regulatory role for VIP in digestive and smooth muscle function. When VIP, or a closely related peptide, was subsequently detected by radioimmunoassay and immunofluorescence throughout the gastrointestinal tract and later in the adrenals, in distinct areas of the brain (e.g. cerebral cortex and hypothalamus) and peripheral nerves, the possible physiological role of this compound had to be reexamined. The assumption that it may function as a neurotransmitter was an auxiliary hypothesis. The wide distribution of VIP (or VIP-like peptides) in different organs and the multiplicity of its actions suggests a possible alternative, namely that VIP could be a prohormone.

The concept of prohormone was established through the discovery of proinsulin by Stein et al, *Proc. Nat. Acad. Sci. USA*, 57, p. 473 (1967). Conversion of proinsulin to insulin takes place by enzymic hydrolysis which cleaves the chain at two points, and also removes the two pairs of basic amino acids which are at the C-terminus of the newly formed fragments. An inspection of the sequences of both porcine and avian VIP reveals a certain analogy with respect to the distribution of basic amino acids. Two pairs of such residues occur in VIP as well, Arg-Lys in positions 14, 15 and Lys-Lys in positions 20 and 21. It is tempting to assume a specific enzymic cleavage of VIP similar to the one that occurs with proinsulin and to hypothesize hormonal functions for the resulting fragments. To test this hypothesis several potential fragments were synthesized.

The design of VIP-fragments was guided by the pattern of conversion of insulin to proinsulin. An analogous enzymic cleavage of VIP between residues 15 and 16 and removal of the pair of basic residues from the C-terminus of the newly formed N-terminal fragment should produce two 13-peptides, $VIP_{1-13}$ and $VIP_{16-28}$. Further fragmentation of the latter between residues 21 and 22, followed by similar degradation could result in the 4-peptide $VIP_{16-19}$ and the 7-peptide $VIP_{22-28}$. Accordingly, the present invention includes the preparation of the peptides with sequences $VIP_{16-19}$, $VIP_{16-28}$, and $VIP_{22-28}$. Of these $VIP_{16-19}$ was obtained by conventional methods; $VIP_{22-28}$ (in protected form) was available as an intermediate of the synthesis of $VIP_{16-28}$ and also in previous syntheses of VIP peptides, reported by Bodanszky et al, *Biorg. Chem.* 5, p. 339 (1976).

In the exaples of this application, there are described the syntheses of chicken VIP segments $VIP_{17-19}$, $VIP_{16-19}$, $VIP_{16-20}$, and $VIP_{16-28}$. The $VIP_{16-28}$ segment or 13-member peptide was secured by the condensation of two segments, t-butyloxy-carbonyl-L glutaminyl-L-methionine, and the 11-peptide L-alanyl-L-valyl-N$^\epsilon$-t-butyloxycarbonyl-L-lysyl-N$^\epsilon$-t-butyloxycarbonyl-L-lysyl-L-tyrosyl-L-leucyl-L-asparaginyl-0-t-butyl-L-seryl-L-valyl-L-leucyl-L-threoninamide. This 11-peptide derivative was built stepwise by the method of Bodanszky, *Am. N.Y. Acad. Sci.*, 88, p. 655 (1960) with active esters as reactive derivatives of the constituent amino acid residues. The benzyloxycarbonyl group was used for α-amino protection and hydrogenolysis in the presence of a tertiary amine for partial deprotection. Final removal of protecting groups by acidolysis yielded the trifluoroacetate salt of the 13-peptide amide $VIP_{16-28}$. The inherent lability caused by the N-terminal glutaminyl residue prompted the conversion of a major portion of the product to the corresponding pyroglutamyl peptide. This was done also in the expectation that a peptide with pyroglutamic acid as N-terminal residue is more suitable for biological tests than the analogous glutamine derivative because it is resistant to common aminopeptidases. In fact, pyroglutamic acid is the N-terminal residue of several biologically active peptides such as gastrins, caerulein, TRH, LH-RH, etc. The peptides $VIP_{17-19}$, $VIP_{16-19}$, and $VIP_{16-20}$ were prepared using similar procedures. The free peptides are obtained by conventional procedures in removing protecting groups from side chains, C-terminal, N-terminal positions, and salt forms.

The present invention thus provides the following novel polypeptides:

(1) The free peptide, C-terminal amide, and L-pyroglutamyl derivative of $VIP_{17-19}$ having the following amino acid sequence:

Met-Ala-Val (2) The free peptide C-terminal amide, and L-pyroglutamyl derivative of $VIP_{16-19}$ having the following amino acid sequence:

Met-Ala-Val-Lys (3) The free peptide, and C-terminal amide of $VIP_{16-20}$ having the following amino acid sequence:

Gln-Met-Ala-Val-Lys (4) The free peptide and C-terminal amide of $VIP_{16-28}$ having the following amino acid sequence:

X-Met-Ala-Val-Lys-Lys-Tyr-Leu-Asn-Ser-Y-Leu-Z, wherein X is Gln or pyroglutamyl, Y is Val or Ile and Z is Thr or Asn.

The polypeptides of this invention may be generically described by general formula as follows:

(a) X-Met-Ala-Val-Lys-Lys-Tyr-Leu-Asn-Ser-Y-Leu-Z-$X_1$, wherein X is hydrogen, Gln, or pyroglutamyl, and $X_1$ is OH or $NH_2$; Y is Val or Ile, and Z is Asn or Thr; and (b) $X_{(0-1)}$-Met-Ala-Val-(Lys)$_{0-1}$-$X_1$, wherein X is hydrogen, glutamyl, or pyroglutamyl, and $X_1$ is OH or $NH_2$.

These compounds have pharmacological characteristics like and unlike the 28-member vasoactive peptides described in U.S. Pat. Nos. 4,119,118, 3,862,927, and 4,016,258. Uniquely, they appear to have hormonal activity whereas the vasoactive peptides are prohormones. They are also useful as intermediates for the preparation of the 28-member chicken peptide described in U.S. Pat. No. 4,016,258 and porcine peptide described in U.S. Pat. Nos. 4,119,118 and 3,862,427, by extending the polypeptide chain using standard techniques described for example by Bodanszky, Klausner, and Ondetti in "Peptide Synthesis", Second Edition; John Wiley & Sons, (1976).

EXPERIMENTAL

In the following example, the various derivatives, protecting groups, reagents, solvents, etc. are referred to by abbreviation for convenience as follows:

| Derivatives; Protecting Groups; Reagents; Solvents | Abbreviated Designation |
| --- | --- |
| Nitro | $NO_2$ |
| Benzyl | BZL |
| Tertiary-butyloxycarbonyl | tBOC |
| Tertiary-amyloxycarbonyl | AOC |
| N-hydroxysuccinimide ester | OSu |
| Methyl ester | OMe |
| Trifluoroacetic acid | TFA |
| Dicyclohexylcarbodiimide | DCC |
| Ethyl ester | OEt |
| Benzyloxycarbonyl | Z |
| Dimethylformamide | DMF |
| Tetrahydrofuran | THF |
| p-Nitrophenyl ester | ONP |
| 2,4-Dinitrophenyl ester | ODNP |
| 1-ethoxycarbonyl-2-ethoxy-1,2-dihydroquinoline | EEDQ |

In the following examples, parts are by weight unless otherwise indicated. In addition, the capillary melting points are reported uncorrected. On tlc spots were revealed by charring, ninhydrin or fluorescamine or by t-butyl hypochlorite-KI-starch reagent. The following solvent systems were used on silica gel plates: A, $CHCl_3$-MeOH (9:1); B, $CHCl_3$-MeOH (8:2); C, n-BuOH-AcOH-$H_2O$ (4:1:1); D, benzene-EtOAc (19:1); E, EtOH-$H_2O$ (7:3); F, t-AmOH-iso-PrOH-$H_2O$ (51:21:28).

For amino acid analysis, samples were hydrolyzed with constant boiling hydrochloric acid in evacuated, sealed ampoules at 110° for 16 hr and analyzed on a Beckman-Spinco 102C instrument. The $NH_3$ values were reported uncorrected for blanks.

EXAMPLE 1

Benzyloxycarbonyl-L-valyl-L-leucyl-L-threonine methyl ester (II)

Benzyloxycarbonyl-L-leucyl-L-threonine methyl ester (I, 3.8 g, 10 mmole) was dissolved in a mixture of 95% EtOH (50 ml) and 1 N HCl (10 ml) and hydrogenated in the presence of a 10% Pd on charcoal catalyst (0.8 g). After removal of the catalyst and the solvent the residue was dissolved in DMF (35 ml), treated with DIEA (1.6 ml, 10 mmole), benzyloxycarbonyl-L-valine p-nitrophenyl ester (4.3 g, 12 mmole) and HOBt (1.5 g, 10 mmole). After a negative spot test with ninhydrin indicated the completion of the reaction, the solvent was removed in vacuo and the residue triturated with $CHCl_3$ (40 ml). The resulting solid was washed with $CHCl_3$ (20 ml) and dried: 4.5 g (94%, mp 217°-8° C.,) unchanged after extraction with solvents, $[\alpha]_D^{24}$ −11.7° (c 1.5, DMF); R$_f$C 0.75; Thr 1.08; Val 0.98; Leu 1.0.

Anal. Calcd for $C_{24}H_{37}N_3O_7$ (479.6): C, 60.1; H, 7.8; N, 8.8. Found: C, 59.9; H, 7.7; N, 8.8.

EXAMPLE 2

N-Benzylocycarbonyl-O-t-butyl-L-seryl-L-valyl-L-leucyl-L-threonin-amide (IV)

A solution of the protected 3-peptide methyl ester II (3.5 g, 7.3 mmole) in MeOH (500 ml) was cooled in an ice-water bath while a stream of $NH_3$ was passed through it. After 1 hour the flask was stoppered and kept at room temperature overnight. The protected 3-peptide amide (III) was collected by filtration, washed with $CH_3OH$ and dried: 2.7 g (79%) m.p. 240°-242° C; R$_f$A, 0.24. A second crop (0.4 g, m.p. 238°-242°) obtained from the filtrate and washings was not used in the next step.

A sample of compound III (1.4 g, 3 mmole) was hydrogenated in a mixture of DMF (40 ml) and DIEA (2 ml) in the presence of palladium black (0.10 g) in a closed system. After 20 hr the catalyst was removed and the solution concentrated in vacuo to ca 30 ml, and treated with N-benzyloxycarbonyl-O-t-butyl-L-serine pentachlorophenyl ester (1.93 g, 3.6 mmole), HOBt (1.5 g, 3 mmole) and DIEA (0.48 ml, 3 mmoles). After about 20 min. the ninhydrin spot-test was negative. The solvent was removed in vacuo and trituration of the residue (a gel) with ether (30 ml) yielded a solid which was reprecipitated from DMF with ether. The product (homogeneous on tlc, system A) weighed 1.56 g (86%); m.p. 215°-218°. For analysis a sample was once more reprecipitated from DMF with ether:

m.p. 217°-219°; $[\alpha]_D^{24}$ −1.0° (c 2, DMF); R$_f$A, 0.32; R$_f$C, 0.66; Thr, 0.97; Ser, 1.06; Val, 1.0; Leu, 1.0.

Anal. Calcd for $C_{30}H_{49}N_5O_8$ (607.7): C, 59.3; H, 8.1; N, 11.5. Found C, 59.0; H, 8.0; N, 11.4.

EXAMPLE 3

Benzyloxycarbonyl-L-asparaginyl-O-t-butyl-L-seryl-L-valyl-L-leucyl-L-threoninamide (V)

Compound IV (1.5 g, 2.57 mmole) was hydrogenated in DMF (30 ml) in the presence of DIEA (1.8 ml) and a palladium black catalyst (0.10 g). The filtrate from the catalyst was concentrated in vacuo to ca 25 ml and treated with Z-L-Asn-ONp (1.49 g, 3.85 mmole). On standing at room temperature overnight the reaction went to completion (tlc). During the concentration the mixture formed a semisolid mass. This was treated with EtOAc (30 ml), filtered washed with EtOAc and dried: 1.69 g (91%) m.p. 263°-266° C. dec.; $[\alpha]_D^{24}$ −11.3° (c 2, DMF); R$_f$A, 0.10; R$_f$C, 0.54. Asp, 1.02; Thr, 0.98; Ser, 0.97; Val, 1.0; Leu, 1.0.

Anal. Calcd for $C_{34}H_{55}N_7O_{10}$ (721.8) C, 56.6; H, 7.7; N, 13.6. Found: C, 56.6; H, 7.9; N, 13.4.

EXAMPLE 4

Benzyloxycarbonyl-L-leucyl-L-asparaginyl-O-t-butyl-L-seryl-L-valyl-L-leucyl-L-threoninamide (VI)

Hydrogenation of compound V (1.68 g, 2.33 mmole) in DMF (50 ml) in the presence of DIEA (1.6 ml) and a palladium black catalyst (0.1 g) was followed by filtration and concentration in vacuo to ca 20 ml. The amine was treated with Z-L-Leu-ONp (1.31 g, 3.4 mmole) overnight.

The semisolid mixture was diluted with EtOAc (60 ml), filtered, washed with EtOac and dried: 1.86 g (95%), dec. at about 265° C; $[\alpha]_D^{24}$ −15.5° (c 1,5, DMF); R$_f$C, 0.67; R$_f$D, 0.44. Asp, 0.96; Thr, 0.93; Ser, 0.92; Val, 1.01; Leu, 2.0.

Anal. Calcd for $C_{40}H_{66}N_8O_{11}$ (835.0): C, 57.5; H, 8.0; N, 13.4. Found: C, 57.3; H, 7.8; N, 12.9.

EXAMPLE 5

Benzyloxycarbonyl-L-tyrosyl-L-leucyl-L-asparaginyl-O-t-butyl-L-seryl-L-valyl-L-leucyl-L-threoninamide (VII)

Compound VI (0.48 g, 1 mmole) was hydrogenated in DMF (50 ml) in the presence of DIEA (1.3 ml) and palladium black (60 mg) and after the removal of the catalyst the solution was concentrated to ca 10 ml. Z-L-Tyr-ONp (0.57 g, 1.3 mmole) was added and the mixture kept overnight at room temperature. The resulting gel was triturated with EtOAc (30 ml) to yield a solid, 0.92 g (92%) m.p. 261°–263° C. dec.; $R_fA$, 0.42; $R_fC$, 0.70; Asp, 1.01; Thr, 0.46; Ser, 0.43; Val, 1.04; Leu, 2.0; Tyr, 0.87.

Anal. calcd for $C_{49}H_{75}N_9O_{13}$ (998.2): C, 59.0; H, 7.6; N, 12.6. Calcd for $C_{49}H_{75}N_9O_{13}.H_2O$ (1016.2): C, 57.9; H, 7.6; N, 12.4. Found: C, 57.5; H, 7.8; N, 12.3.

EXAMPLE 6

$N^\alpha$-Benzyloxycarbonyl-$N^\epsilon$-t-butyloxycarbonyl-L-lysyl-L-tyrosyl-L-leucyl-L-asparaginyl-O-t-butyl-L-seryl-L-valyl-L-leucyl-L-threoninamide (VIII)

Starting with hydrogenation of counpound VII (0.915 g, 0.92 mmole) in DMF (40 ml) and DIEA (0.7 ml) in the presence of Pd-black (70 mg) the title compound was prepared by acylation with Z-L-Lys(Boc)-ONp (0.60 g, 1.2 mmole). The reaction was complete in 2 days. Trituration of the mixture (a gel) with EtOAc (30 ml) and washing of the precipitate with EtOAc and with ether yielded 1.10 g (98%) of VIII, m.p. 251°–253° C. dec.; $R_fB$, 0.43; $R_fC$, 0.71; Asp, 1.09; Thr, 1.03; Ser, 1.0; Val, 1.02; Leu, 2.0; Tyr, 0.78.

Anal. calcd for $C_{60}H_{95}N_{11}O_{16}$ (1226.5): C, 58.8; H, 7.8; N, 12.6. Found: C, 58.6; H, 7.8; N, 12.3.

EXAMPLE 7

$N^\alpha$-Benzyloxycarbonyl-$N^\epsilon$-t-butyloxycarbonyl-L-lysyl-$N^\epsilon$-t-butyloxy-carbonyl-L-lysyl-L-tyrosyl-L-leucyl-L-asparaginyl-O-t-butyl-L-seryl-L-valyl-L-leucyl-L-threoninamide (IX)

The protected 8-peptide VIII (1.1 g, 0.9 mmole) was hydrogenated as described above, in DMF (40 ml) in the presence of DIEA (0.7 ml). Hydrogenation took 72 hr to completion and hence each day more catalyst was added (a total 170 mg). After the removal of the catalyst and concentration to about 15 ml, the solution was treated with the active ester of lysine mentioned above (0.6 g, 1.2 mmole), HOBt and DIEA (both 0.4 mmole) were added to catalyze the acylation. The reaction still required 3 days for completion. The thick gel was triturated with EtOAc and dried; 1.78 g (97%) decomposing without melting at 247°–252° C; $R_fB$, 0.41; $R_fC$, 0.72; Asp, 0.99; Thr, 0.95; Ser, 0.91; Val, 0.95; Leu, 2.0; Tyr, 0.88; Lys, 2.1.

Anal. calcd for $C_{71}H_{115}N_{13}O_{19}$ (1454.7): C, 58.6; H, 8.0; N, 12.5. Calcd for $C_{71}H_{115}N_{13}O_{19}.H_2O$ (1472.7): C, 57.9; H, 8.0; N, 12.4. Found: C, 57.2; H, 8.0; N, 12.3.

EXAMPLE 8

Benzyloxycarbonyl-L-valyl-$N^\epsilon$-t-butyloxycarbonyl-L-lysyl-$N^\epsilon$-t-butyloxycarbonyl-L-lysyl-L-tyrosyl-L-leucyl-L-asparaginyl-O-t-butyl-L-seryl-L-valyl-L-leucyl-L-threoninamide (X).

The 9-peptide derivative IX (1.76 g, 0.86 mmole) was dissolved in DMF (25 ml) DIEA (1.3 ml) and Pd-black (0.10 g) were added and the mixture hydrogenated for about 4 hr. Removal of the catalyst and concentration of the solution to ca 15 ml was followed by the addition of Z-L-Val-ONp (0.67 g, 1.8 mmole) HOBt (0.12 g, 0.9 mmole) and DIEA (0.15 ml. 0.9 mmole). After overnight at room temperature acylation was complete (tlc system B). Trituration of the gel with ether (200 ml) yielded 1.11 g (81%), no m.p. could be be observed up to 300°; $R_fB$, 0.39; $R_fC$, 0.73.

Anal. Calcd for $C_{76}H_{124}N_{14}O_{20}$ (1553.9): C, 58.7; H, 8.0; N, 12.6. Calcd for $C_{76}H_{124}N_{14}O_{20}.H_2O$ (1589.9): C, 57.4; H, 8.1; N, 12.3. Found: C, 57.2; N, 8.0; N, 12.7.

EXAMPLE 9

Benzyloxycarbonyl-L-alanyl-L-valyl-$N^\epsilon$-t-butyloxycarbonyl-L-lysyl-$N^\epsilon$-t-butyloxycarbonyl-L-lysyl-L-tyrosyl-L-leucyl-L-asparaginyl-O-t-butyl-L-seryl-L-valyl-L-leucyl-L-threoninamide (XI)

Compound X (1.55 g, 0.97 mmole) was hydrogenated in DMF (100 ml) in the presence of DIEA (5 ml) and Pd-black (0.10 g) overnight. The catalyst and about ⅔ of the solvent were removed and acylation of the resulting amine was carried out with Z-L-Ala-ONp (0.73 g, 2.1 mmole, Fox), HOBt and DIEA (1 mmole each). After overnight at room temperature the reaction was complete (tlc). The mixture was diluted with ether and washed with ether (total of 1 liter). The dried material, 1.34 g (84%) (Asp, 0.90; Thr, 0.90; Ser, 0.80; Ala, 1.10; Val, 1.40; Leu, 2.00; Tyr, 1.0; Lys, 1.90) was too insoluble for tlc or for purification and gave not entirely satisfactory values on elemental analysis.

Anal. Calcd for $C_{79}H_{129}N_{15}O_{21}$ (1624.9): C, 58.4; H, 8.0; N, 12.9. Found: C, 57.8; H, 7.9; N, 13.3.

EXAMPLE 10 tert-Butyloxycarbonyl-L-glutaminyl-L-methionine (XII)

A solution of Boc-L-Gln (Bachem, 4.92 g, 20 mmole) in THF (45 ml) was cooled to −15°, neutralized with N-methylmorpholine (2.2 ml, 20 mmole) and treated with isobutylchlorocarbonate 2.74 g (20 mmole). After 5 min a solution of L-methionine (4.48 g, 30 mmole) and N-methylmorpholine (3.3 ml. 30 mmole) in $H_2O$ (45 ml) was added. (Some warming was necessary to obtain a clear solution of the methionine salt). The mixture was stirred and allowed to warm up to room temperature; gradually a clear solution formed. After 1.5 hr the solution was concentrated in vacuo to remove most of the THF and then acidified with a 20% solution of citric acid in $H_2O$. Saturation with NaCl and extraction with EtOAc (3×50 ml), was necessary to isolate the desired material. The organic layer was washed with $H_2O$ and evaporated with a stream of $N_2$. The solid residue was suspended in warm EtOAc (100 ml), stirred for 1 hr, filtered, washed with EtOAc and dried. The product (4.75 g, 63%) melted at 149°–150°; $[\alpha]_D^{20}$ −11.8° (c 2, DMF); $R_fB$, 0.60; $R_fE$, 0.73, Glu, 1.0; Met, 1.0. The proton nmr spectrum, in $CD_3COOD$, showed the expected resonances.

Anal. calcd for $C_{15}H_{27}N_3O_6S.H_2O$ (395.5): C, 45.5; H, 7.4; N, 10.6. Found: C, 45.3; H, 6.9; N, 10.6.

EXAMPLE 11

L-Pyroglutamyl-L-methionyl-L-alanyl-L-valyl-L-lysyl-L-lysyl-L-tyrosyl-L-leucyl-L-asparaginyl-L-seryl-L-valyl-L-leucyl-L-threoninamide (XIII)

To a solution of compound XII (0.113 g, 0.3 mmole) and partially deprotected (by hydrogenation as described in previous paragraphs) compound XI (0.37 g, 0.35 mmole) in DMF (12 ml) HOBt (34 mg, 0.25 mmole) and DCC (0.5 ml of a 0.55 M solution in DMF) were added. After one day at room temperature EtOAc (20 ml) was added, the precipitate collected by centrifugation, washed with EtOAc, 95% EtOH, ether and once more with EtOAc. The dried product weighed 0.38 g, no m.p. to 300° C., R$_f$B, 0.68; R$_f$F, 0.62.

A sample of the protected 13-peptide amide (0.15 g) was dissolved in TFA (ca 3 ml) containing 10% anisole. After 50 min at room temperature the solution was evaporated to dryness in vacuo, the residue triturated with ether, with EtOAc and dried: 0.15 g, not melting up to 250°; Asp, 0.96; Thr, 0.90; Ser, 0.88; Glu, 0.94; Ala, 1.1; Val, 2.04; Met, 0.87; Leu, 2.00; Tyr, 0.90; Lys, 2.1.

Anal. calcd for $C_{67}H_{116}N_{18}O_{18}S \cdot 3CF_3COOH$ (1835.8): C, 47.8; H, 6.5; N, 13.7. Found: C, 47.5; H, 6.7; N, 13.5.

Notwithstanding the satisfactory amino acid analysis and elemental analysis the 13-peptide with glutamine as N-terminal residue showed two spots on tlc (cellulose, system C), one presumably the pyroglutamyl derivative. Therefore, the crude material was converted to the pyroglutamyl peptide by dissolving a sample (0.13 g) in 2 N AcOH (10 ml) and storing the solution at room temperature for 6 days. The solution was evaporated to dryness in vacuo and the residue distributed in an automatic Craig apparatus (3 ml phases) in the solvent system n-BuOH-EtOH-1% AcOH (5:1:4) through 201 transfers. A minor peak (K=0.14) and a major peak (K=0.72) were detected by absorption at 275 nm. Compound XIII was secured by concentration in vacuo of the contents of tubes No. 70 to 100 to a small volume and lyophilization. The purified 13-peptide (62 g, di-trifluoroacetate salt) gave a single spot on tlc (cellulose, R$_f$C, 0.70) and also on paper chromatograms ran with the upper phase of the solvent system used for countercurrent distribution. The u.v. spectrum of XIII in H$_2$O corresponded to that of tyrosine; Asp, 0.93; Thr, 0.86; Ser, 0.86; Glu, 0.97; Ala, 1.1; Val, 1.9; Met, 1.0; Leu, 2.00; Tyr, 0.97; Lys, 2.03; NH$_3$, 2.8. For analysis a sample was dried over P$_2$O$_5$ at 60° in vacuo (ca 0.1 mm) for 4 hr. Nevertheless, the analysis indicates retention of acetic acid.

Anal. calcd for C, 48.8; H, 6.8; N. 12.2. Found: C, 48.7; H. 6.8; N, 12.0.

EXAMPLE 12

N$^\alpha$-Benzyloxycarbonyl-N$^\epsilon$-t-butyloxycarbonyl-L-lysinamide (XIV)

A stream of NH$_3$ was passed over a solution of Z-Lys(Boc)ONp (10.2 g, 2.0 mmole, Bachem) in THF (200 ml) for about 3 hr. A precipitate formed. The solvent was removed and the residue triturated and thoroughly washed with ether. The dried protected amide weighed 5.8 g (75%), m.p. 140°-142°, $[\alpha]_D^{24}$ +1.9° (c 1.3. DMF): R$_f$B, 0.54; R$_f$G, 0.54.

Anal. calcd for $C_{19}H_{29}N_3O_5$ (379.4): C, 60.2; H, 7.7; N, 11.0. Found: C, 60.4; H, 7.9; N, 11.1.

EXAMPLE 13

Benzyloxycarbonyl-L-valyl-N$^\epsilon$-t-butyloxycarbonyl-L-lysinamide (XV)

A sample of compound XIV (3.87 g, 10 mmole) was dissolved in MeOH (100 ml), H$_2$O (11 ml), AcOH (1 ml) and a 10% Pd on charcoal catalyst (0.30 g) were added and the mixture hydrogenated for 4 hr. At this time no more starting material could be detected on tlc. The catalyst and solvent were removed and the residue dried in vacuo.

The partially deprotected amide (R$_f$C, 0.50) was dissolved in DMF (50 ml) cooled in an ice-water bath and treated with DIEA (3.5 ml. 22 mmole), HOBt (1.55 g, 10 mmole) and Z-L-Val-ONp (4.25 g, 11 mmole, Bachem). After ½ hr cooling the mixture was kept at room temperature overnight. The solution turned into a semisolid mass, yet it was concentrated in vacuo and then triturated with EtOAc, with ether, filtered, washed with the same solvents and dried: 4.6 g (96%), m.p. 199°-201°; $[\alpha]_D^{24}$ −9.6° (c 0.8, DMF); R$_f$B, 0.48; R$_f$H, 0.33.

Anal. Calcd for $C_{24}H_{38}N_4O_6$ (478.6): C, 60.2; H, 8.0; N, 11.7. Found: C, 59.9; H, 8.1; N, 11.7.

EXAMPLE 14

Benzyloxycarbonyl-L-alanyl-L-valyl-N$^\epsilon$-t-butyloxycarbonyl-L-lysinamide (XVI)

A sample of compound XV (4.3 g, 9 mmole) was hydrogenated as described in the previous paragraph and the partially deblocked peptide (R$_f$C, 0.60) was acylated with Z-L-Ala-ONp (3.47 g, 10 mmole, Bachem) in the presence of DIEA (3.2 ml, 20 mmole) and HOBt (1.3 g, 9 mmole). The product isolated as described for XV weighed 4.2 g (85%) m.p. 214°-217° C., $[\alpha]_D^{24}$ −9.5° (c 0.8, DMF); R$_f$B, 0.48; R$_f$I, 0.33.

Anal. calcd for $C_{27}H_{43}N_5O_7$ (549.7): C, 59.0; H, 7.9; N, 12.7. Found: C, 59.0; H, 7.9; N, 12.7.

EXAMPLE 15

Biphenylisopropyloxycarbonyl-L-methionyl-L-alanyl-L-valyl-N$^\epsilon$-t-butyloxycarbonyl-L-lysinamide (XVII)

Partial deprotection of compound XVI (2.5 g, 4.5 mmole) was carried out by hydrogenation as described above. The free amine, dissolved in DMF (25 ml) containing N-methylmorpholine (0.65 ml, 5.4 mmole) was acylated with the mixed anhydride prepared from BpOC-L-Met (ca 5 mmole), N-methylmorpholine (0.65 ml, 5.4 mmole) in THF (25 ml) at −15° to −20° C. with isobutyl chlorocarbonate (0.70 ml, 5 mmole). After 1 hr at ca −15° the mixture was allowed to warm up to room temperature. Stirring was continued overnight and the reaction maintained basic by addition of N-methylmorpholine. The solvents were removed in vacuo and the residue triturated with a saturated solution of NaHCO$_3$, then with H$_2$O, with EtOAc and finally with ether. After drying 3.2 g was obtained (90%), m.p. 189°-192° C., $[\alpha]_D^{24}$ −11.7° (c −1.2, DMF); R$_f$B, 0.60; R$_f$I, 0.30.

EXAMPLE 16 t-Butyloxycarbonyl-t-glutaminyl-L-methionyl-L-alanyl-L-valyl-N$^\epsilon$-t-butyloxycarbonyl-L-lysinamide (XVIII)

The protected 4-peptide amide XVII (2.66 g, 3.4 mmole) was treated with 80% AcOH (50 ml) overnight. Evaporation of the solvent in vacuo and trituration of the residue with ether afforded the partially deprotected product (R$_f$C, 0.49; R$_f$J, 0.21) which was dissolved in DMF (30 ml) and allowed to react with Boc-L-Gln-ONp (1.39 g, 3.8 mmole, Vega-Fox) in the presence of DIEA (1.3 ml, 8 mmole) and HOBt (0.58 g, 3.8 mmole). After 5 hr most of the solvent was removed in vacuo from the semisolid mass and the residue was triturated with EtOAc and with ether. The product was filtered, dissolved in DMF and reprecipitated by the addition of H$_2$O. After overnight storage in the cold the protected 5-peptide amide was collected, washed with H$_2$O and dried in vacuo: 2.3 g (87%) m.p. 241°-243°;

[α]$_D^{24}$ −22.7° (c 0.9, DMF); R$_f$J, 0.34; R$_f$K, 0.30; R$_f$I, 0.23.

Anal. calcd for C$_{34}$H$_{62}$N$_8$O$_{10}$S (775.0): C, 52.7; H, 8.1; N, 14.5. Calcd for C$_{34}$H$_{62}$N$_8$O$_{10}$S.: C, 52.7; H, 8.0; N, 14.5. Found: C, 2.5; H, 8.2; N, 14.3.

EXAMPLE 17

L-Pyroglutamyl-L-methionyl-L-alanyl-L-valyl-L-lysinamide (XIX)

A sample of the protected 5-peptide amide XVIII (1.0 g, 1.28 mmole) was dissolved in TFA (20 ml) containing acetyl-DL-methionine n-butyl ester (2 g). After 40 min at room temperature the solution was concentrated in vacuo to about 10 ml and diluted with ether (200 ml). The precipitate was thoroughly washed with EtOAc and with ether and dried in vacuo. The 5-peptide amide di-trifluoroacetate salt had no well defined m.p., it gradually decomposed between 200° and 235°. In addition to the main component (R$_f$M, 0.77) two faint spots appeared on tlc, one, presumably the pyroglutamyl derivative XIX, with R$_f$M, 0.46, the second, near the origin, probably the S-t-butylsulfonium salt.

This crude 5-peptide amide (0.40 g) was dissolved in a 8:2 mixture of AcOH-H$_2$O (8 ml) and heated to boiling for 3 min. The solution was cooled to room temperature, and the pyroglutamyl derivative secured by dilution with ether and dried: 0.32 g, m.p. 230°–235° C.; [α]$_D^{24}$ −13.0° (c 0.9 DMF); R$_f$C, 0.15; R$_f$M, 0.46. Glu, 0.97; Ala, 1.03; Val, 1.03; Met, 0.96.

Anal. Calcd for C$_{24}$H$_{43}$N$_7$O$_6$S.CF$_3$COOH (641): C, 46.5; H, 6.6; N, 14.3.

EXAMPLE 18 t-Butyloxycarbonyl-L-valyl-N$^\epsilon$-benzyloxycarbonyl-L-lysine benzyl ester (XX)

N$^\alpha$-t-butyloxycarbonyl-N$^\epsilon$-benzyloxycarbonyl-L-lysine (5.8 g, 15 mmole, Bachem) was converted to the cesium salt, and this salt allowed to react with benzyl bromide (20 mmole). The benzyl ester was purified by chromatography on a silica gel column (100 g), eluted with a 3:2 mixture of CHCl$_3$-hexane followed by CHCl$_3$-CH$_3$OH (19:1). The purified material, an oil, weighed 5.6 g (79%), R$_f$N, 0.36; R$_f$in CHCl$_3$, 0.10. The nmr spectrum in CDCl$_3$ corresponded to the one expected for the benzyl ester.

This material (4.67 g, 9.9 mmole) was dissolved in a 7:3 mixture of TFA-AcOH (15 ml). After 40 min at room temperature the solution was evaporated to dryness in vacuo and the residue dried in a desiccator over KOH pellets. On tlc (R$_f$C, 0.75) no starting material could be detected. The trifluoroacetate salt was dissolved in DMF, cooled in an ice-water bath while DIEA (3.2 ml, 20 mmole), HOBt (1.53 g, 10 mmole) and Boc-L-Val-ONp (3.72 g, 11 mmole, Bachem) were added. After standing overnight at room temperature the solution was removed in vacuo, the residue triturated with a 8:2 mixture of ether and EtOAc, the precipitate washed with ether and dried, 1.6 g. From the combined filtrate and washings a second crop (2.3 g) of the same quality was obtained through chromatography on a silica gel (100 g) column. For elution CHCl$_3$ and then a 19:1 mixture of CHCl$_3$-CH$_3$OH were used. The two crops amounted to 3.9 g (69%); m.p. 120°–122° C.; [α]$_D^{26}$ −12.7° (c 0.1, DMF) R$_f$ (ether), 0.54; R$_f$K 0.65 CHCl$_3$-CH$_3$OH, 0.27.

Anal. calcd for C$_{31}$H$_{43}$N$_3$O$_7$ (569.7): C, 65.4; H, 7.6; N, 7.4. Found: C, 65.6; H, 7.7; N, 7.6.

EXAMPLE 19 t-Butyloxycarbonyl-L-alanyl-L-valyl-N$^\epsilon$-benzyloxycarbonyl-L-lysine benzyl ester (XXI)

The Boc group was removed from a sample (3.8 g, 6.6 mmole) of compound XX as described above. The partially deprotected 2-peptide ester (trifluoroacetate salt) was dissolved in DMF (60 ml) and treated with DIEA (2.4 ml, 15 mmole), HOBt (1.18 g, 7.7 mmole) and Boc-L-Ala-ONp (2.38 g, 7.7 mmole, Bachem) at 0°. After overnight storage at room temperature a semi-solid mass formed. Most of the solvent was removed in vacuo, the residue triturated with EtOAc and with ether and dried: 3.6 g (85%), m.p. 140°–143° C.; [α]$_D^{23}$ −21.8° (c 0.8 DMF); R$_f$B, 0.85; R$_f$I, 0.62.

Anal. calcd for C$_{34}$H$_{48}$N$_4$O$_8$ (640.8): C, 63.7; H, 7.6; N, 8.7. Calcd for C$_{34}$H$_{48}$N$_4$O$_8$.H$_2$O (658.8): C, 62.0; H, 7.6; N, 8.5. Found: C, 61.6; H, 7.3; N, 8.3.

EXAMPLE 20 t-Butyloxycarbonyl-L-methionyl-L-alanyl-L-valyl-N$^\epsilon$-benzyloxycarbonyl-L-lysine benzyl ester (XXII)

Partial deprotection of compound XXI (3.4 g, 5.3 mmole) was carried out as described in the previous paragraph. The trifluoroacetate salt (R$_f$C, 0.75) was acylated in DMF (50 ml) with Boc-L-Met-ONp (2.18 g, 5.9 mmole, Bachem) in the presence of DIEA (1.9 ml, 12 mmole) and HOBt (0.9 g, 5.9 mmole). After 4 hr at room temperature the reaction was complete. Evaporation of most of the solvent in vacuo was followed by trituration with EtOAc. The precipitate was washed with EtOAc, with ether and dried: 3.8 g (93%); m.p. 169°–171° C., [α]$_D^{24}$ −21.5° (c 1.2, DMF) R$_f$K, 0.65; R$_f$I, 0.52.

Anal. calcd for C$_{39}$H$_{57}$N$_5$O$_9$S (771.9): C, 60.7; H, 7.5; N, 9.1. Found: C, 60.8; H, 7.4; N, 9.3.

EXAMPLE 21 t-Butyloxycarbonyl-L-glutaminyl-L-methionyl-L-alanyl-L-valyl-N$^\epsilon$-benzyloxycarbonyl-L-lysine benzyl ester (XXIII)

The Boc group was removed from a sample of compound XXII (2.5 g, 3.3 mmole) as described in previous paragraphs. The trifluoroacetate salt washed with ether and dried; the white solid (R$_f$C, 0.76) showed on tlc a slight impurity at the origin (presumably the t-butylsulfonium salt). This material was acylated with Boc-L-Gln-ONp (1.4 g, 3.8 mmole, Bachem) in the presence of DIEA (1.3 ml, 8 mmole) and HOBt (0.58 ml, 3.8 mmole). Next day the product was isolated as described for XII and then purified by precipitation from a solution in DMF with H$_2$O. The product was washed with H$_2$O and dried: 28 g (93%), m.p. 238°–241° C. [α]$_D^{23}$ −27.7° (c 0.8, DMF); R$_f$K, 0.43; R$_f$L, 0.50.

Anal. calcd for C$_{44}$H$_{65}$N$_7$O$_{11}$S (900.1): C, 58.7; H, 7.3; N, 10.9. Found: C, 58.8; H, 7.4; N, 11.2.

EXAMPLE 22

L-Pyroglutamyl-L-methionyl-L-alanyl-L-valyl-L-lysine (trifluoroacetate salt) (XXIV)

A sample of the protected 5-peptide XXIII (0.50 g, 0.55 mmole) was dissolved in DMF (60 ml), H$_2$O (6 ml), DIEA (6 ml) and 10% Pd/BaSO$_4$ (0.10 g) were added and the mixture hydrogenated for 8 hr. On tlc a single spot (R$_f$C, 0.45; R$_f$L, 0.75) was observed. The black solution was filtered on a layer of Celite, the latter washed with DMF and the filtrates evaporated in vacuo to dryness. The residue was dissolved in TFA (20 ml) containing acetyl-DL-methionine n-butyl ester (1.0 g) and kept at room temperature for ½ hr. The TFA was removed in vacuo and the residue dissolved in a mixture of EtOAc (20 ml) and H$_2$O (20 ml). The aqueous layer was extracted twice with EtOAc (20 ml each), filtered and lyophilized to give a white powder, 0.40 g. In system C the spot remained near the origin; R$_f$M, 0.45. Trace amounts of impurities, probably the pyroglutamyl derivative and the sulfonium salt could also be detected. A sample (0.10 g) was dissolved in AcOH (ca 2 ml) and heated to boiling for 3 min. After cooling the product was precipitated with ether (20 ml). The pyroglutamyl derivative was collected, washed with ether: 80 mg; m.p. 238°–242° C.; R$_f$C, 0.10; R$_f$M, 0.60. Glu, 0.98; Ala, 0.99; Val, 1.01; Met, 0.96.

EXAMPLE 23

Benzyloxycarbonyl-L-alanyl-L-valine tert-butyl ester (XXV)

A solution of L-valine tert-butyl ester hydrochloride (2.1 g, 10 mmole) in DMF (10 ml) was treated with DIEA (1.6 ml. 10 mmole) and benzyloxycarbonyl-L-alanine p-nitrophenyl ester (3.5 g, 10 mmole). After overnight at room temperature, the solution was filtered through a column of neutral Al$_2$O$_3$ (100 g) and eluted with DMF. The solvent was removed in vacuo and the residue filtered through a column of silica gel (50 g) eluted with CHCl$_3$. The resulting oil (3.0 g, 79%) was homogeneous on tlc; R$_f$ (CHCl$_3$) 0.10; R$_f$ (ether) 0.70; R$_f$(CHCl$_3$ 24, CH$_3$OH 1) 0.55.

EXAMPLE 24 tert-Butyloxycarbonyl-L-glutaminyl-L-methionyl-L-alanyl-L-valine tert-butyl ester (XXVI)

Compound XXV (1.67 g, 4.4 mmole) was dissolved in EtOH (40 ml) and hydrogenated in the presence of a 10% Pd on charcoal catalyst (0.20 g). After 4 hr the catalyst and the solvent were removed and the residue (R$_f$CHCl$_3$ 8, CH$_3$OH 2) 0.40; R$_f$C 0.55) was dissolved in DMF (10 ml).

This solution was added to one of compound XII (1.66 g, 4.4 mmole) in DMF (30 ml) followed by HOBt (0.673 g, 4.4 mmole) and DCC (0.96 g, 4.4 mmole). Next day DIEA (4.5 mmole) was added. The reaction went to completion after 2 more days. The precipitated urea derivative was filtered off and the solvent removed in vacuo. The residue was triturated with EtOAc, 0.1 N Na$_2$CO$_3$, H$_2$O, 0.2 N citric acid and H$_2$O. It was dissolved in DMF (10 ml) and filtered. The product was precipitated by the addition of H$_2$O. It was collected and washed with H$_2$O and dried: 1.8 g. A second crop, 0.4 g, separated from the filtrate on cooling overnight. Total yield 87%. Both crops melted at 194°–198°. R$_f$ (CHCl$_3$ 23, MeOH 2) 0.16 R$_f$ (EtOAc 60-pyridine 20-AcOH 6-H$_2$O 11) 0.80; $[\alpha]_D^{23}$ −31° (c 1, DMF).

Anal. calcd for C$_{27}$H$_{49}$N$_5$O$_8$S (603.4): C, 53.7; N, 8.1; N, 11.6. Found: C, 53.6; N, 8.1; N, 11.6.

EXAMPLE 25

L-pyroglutamyl-L-methionyl-L-alanyl-L-valine (XXVII)

A sample of compound XXVI (0.60 g) was dissolved in a mixture of trifluoroacetic acid (10 ml) and anisole (1 ml) and was kept at room temperature for 4 hr. The solvents were removed with a stream of N$_2$, the residue triturated with ether (80 ml), the precipitate collected, washed with ether and dried. It was dissolved in AcOH (6 ml) and heated to boiling for 3 min. After cooling ether (80 ml) was added to the solution (ca 2 ml) and the precipitate collected by centrifugation. It was washed with ether chromatography on silica gel (35×2.5 cm, Baker) in EtOAc-pyridine-AcOH-H$_2$O (60:20:6:11). The purified tetrapeptide recovered from fractions No. 18–27 (15 ml each). In addition to homogeneous material (0.30 g) some slightly contaminated product (0.27 g) was also obtained, the latter from fractions No. 28 and on. The peptide had no well defined m.p., gradually decomposed above 200° C.; $[\alpha]_D^{23}$ −68.5° (C 0.7, H$_2$O); Glu, 1.0; Ala, 0.98; Val, 1.00; Met, 0.99 (100% recovery).

Anal. calcd for C$_{18}$H$_{30}$N$_4$O$_6$S (430.3): C, 50.2; H, 7.0; N, 13.0. Found: C, 50.0; H, 7.1; N, 13.3.

What is claimed is:

1. A new polypeptide selected from the group consisting of those of the following general formulae:
   (a) X-Met-Ala-Val-Lys-Lys-Tyr-Leu-Asn-Ser-Y-Leu-Z-X$_1$
   wherein X is hydrogen, Gln, or pyroglutamyl; X$_1$ is OH or NH$_2$; Y is Val or Ile; and Z is Asn or Thr; and
   (b) (X)$_{0-1}$-Met-Ala-Val-(Lys)$_{0-1}$-X$_1$
   wherein X and X$_1$ are as described above.

2. A polypeptide according to claim 1 wherein X is hydrogen and X$_1$ is OH.

3. A polypeptide according to claim 1 wherein X is pyroglutamyl.

4. A polypeptide according to claim 1 wherein X is hydrogen, X$_1$ is NH$_2$.

5. A polypeptide according to claim 1 wherein X is Gln.

6. A polypeptide according to claim 1 wherein X is pyroglutamyl.

7. A polypeptide according to claim 1 wherein Y is Ile and Z is Asn.

8. A polypeptide according to claim 1 wherein Y is Val and Z is thr.

9. The free polypeptide and C-terminal amide of VIP$_{17-19}$ having the following amino acid sequence:

Met-Ala-Val.

10. The free polypeptide and C-terminal amide of VIP$_{16-19}$ having the following amino acid sequence:

Met-Ala-Val-Lys.

11. The free polypeptide, and C-terminal amide of VIP$_{16-20}$ having the following amino acid sequence:

X-Met-Ala-Val-Lys wherein X is Gln or pyroglutamyl.

12. The free peptide and C-terminal amide of VIP$_{16-28}$ having the following amino acid sequence:

X-Met-Ala-Val-Lys-Lys-Tyr-Leu-Asn-Ser-Y-Leu-Z wherein X is Gln or pyroglutamyl; Y is Val or Ile and Z is Thr or Asn.

13. A polypeptide according to claim 1 of the following amino acid sequence:

Met-Ala-Val.

14. A polypeptide according to claim 1 of the following amino acid sequence:

Met-Ala-Val-Lys.

15. A polypeptide according to claim 1 of the following amino acid sequence:

Gln-Met-Ala-Val-Lys.

16. A polypeptide according to claim 1 of the following amino acid sequence:

Gln-Met-Ala-Vla-Lys-Lys-Tyr-Leu-Asn-Ser-Val-Leu-Thr.

* * * * *